US007479530B2

(12) United States Patent
Hughes et al.

(10) Patent No.: US 7,479,530 B2
(45) Date of Patent: Jan. 20, 2009

(54) POLYMER HAVING CHARGED UNITS

(75) Inventors: Timothy Charles Hughes, Victoria (AU); Grace Yim Ngan Chan, Victoria (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 200 days.

(21) Appl. No.: 10/515,218

(22) PCT Filed: May 21, 2003

(86) PCT No.: PCT/AU03/00611

§ 371 (c)(1),
(2), (4) Date: May 16, 2005

(87) PCT Pub. No.: WO03/097711

PCT Pub. Date: Nov. 27, 2003

(65) Prior Publication Data

US 2005/0228120 A1    Oct. 13, 2005

(30) Foreign Application Priority Data

May 21, 2002    (EP)    .................................. 02011173

(51) Int. Cl.
| C12N 5/00 | (2006.01) |
| C08F 220/10 | (2006.01) |
| C08F 220/14 | (2006.01) |
| C08F 265/04 | (2006.01) |
| C08F 283/01 | (2006.01) |
| A61K 9/14 | (2006.01) |
| C08G 64/00 | (2006.01) |
| C07D 207/46 | (2006.01) |
| C07D 211/94 | (2006.01) |
| C08L 41/00 | (2006.01) |
| A61F 2/44 | (2006.01) |

(52) U.S. Cl. ........................ 526/247; 526/246; 526/248; 526/320; 526/72; 526/274; 526/275; 526/276; 526/277; 526/278; 526/286; 521/149; 521/159; 521/50; 521/82; 521/154; 623/17.16; 435/395; 524/547; 525/292; 525/329.4

(58) Field of Classification Search ................ 526/247, 526/547, 274–278, 286–288; 521/149, 154; 521/159; 435/395; 548/520, 435, 465, 542; 623/17.16; 525/292, 329.4

See application file for complete search history.

(56) References Cited

U.S. PATENT DOCUMENTS

| 3,185,660 | A | * | 5/1965 | Beste | .......................... 524/437 |
| 4,091,165 | A | * | 5/1978 | Hayama | ...................... 428/409 |
| 4,619,965 | A | * | 10/1986 | Ishii et al. | .................... 524/547 |
| 5,122,614 | A | * | 6/1992 | Zalipsky | ...................... 548/520 |
| 5,550,188 | A | * | 8/1996 | Rhee et al. | ................... 525/54.1 |
| 5,994,133 | A | * | 11/1999 | Meijs et al. | .................. 435/395 |
| 6,225,367 | B1 | * | 5/2001 | Chaouk et al. | .............. 521/149 |
| 6,232,430 | B1 | * | 5/2001 | Boonstra et al. | ............ 528/196 |
| 6,428,576 | B1 | * | 8/2002 | Haldimann | ............... 623/17.16 |
| 6,780,942 | B2 | * | 8/2004 | Leon et al. | ................... 525/445 |
| 6,844,028 | B2 | * | 1/2005 | Mao et al. | .................... 427/384 |
| 6,864,350 | B2 | * | 3/2005 | Harris | ........................ 528/322 |
| 2002/0049495 | A1 | * | 4/2002 | Kutryk et al. | ............... 623/1.47 |
| 2006/0160957 | A1 | * | 7/2006 | Muller et al. | ............... 525/292 |

FOREIGN PATENT DOCUMENTS

| GB | 2 303 632 | A |   | 2/1997 |
| GB | 2303632 | A | * | 2/1997 |
| WO | WO 96/31546 |   |   | 10/1996 |
| WO | WO 96/31548 |   |   | 10/1996 |
| WO | WO 97/35904 |   |   | 10/1997 |
| WO | WO 97/35905 |   |   | 10/1997 |
| WO | WO 97/35906 |   |   | 10/1997 |
| WO | WO 00/15686 |   |   | 3/2000 |
| WO | WO 00/29548 |   | * | 5/2000 |
| WO | WO-00/29548 | A2 | * | 5/2000 |

* cited by examiner

*Primary Examiner*—Duane Smith
*Assistant Examiner*—Ives Wu
(74) *Attorney, Agent, or Firm*—Stephen A. Bent; Steven M. Reid; Foley & Lardner LLP

(57) ABSTRACT

A polymer comprising one or more macromonomer units selected from the group consisting of polysiloxane, perfluoroalkylpolyether (PFPE), fluorinated poly(meth)acrylate, polyalkyl (meth)acrylate, polyolefin and fluorinated polyolefin, and one or more charged units (such as an anionic, cationic or zwitter-ionic monomer), formed from a polymerization medium containing an aqueous solution of charged units and use of this polymer as an intraocular lens for the implantation into or onto the cornea. Another aspects relates to a process for coating the above polymer with an adhesive comprising covalently coupling co-reactive surface functional groups of a natural or synthetic polymer with functional groups present (or introduced) on the surface of the macromonomer containing polymer, followed by covalently coupling a multifunctionally activated compound having at least one functional group that is co-reactive to the reactive groups of the natural or synthetic polymer.

35 Claims, No Drawings

POLYMER HAVING CHARGED UNITS

The present invention relates to a biologically compatible polymer. It has particular but not exclusive application as a ready-to-use biomedical device to be fixed to tissue by means of an adhesive. Particularly, the polymer is suitable to form a ready-to-use corneal onlay or inlay, which may be glued under ambient conditions to the corneal basement membrane or corneal stromal tissue.

It is desirable in many applications, especially in the biomaterial and medical field to adhere biomaterials and other materials or devices to tissue. Tissue is defined as any part of the body, living or dead. A biomedical device that can be glued directly to tissue and attains sufficient interfacial bond strength is attractive because it may obviate the need for surgical methods such as suturing. Useful applications include the adhesion of drug delivery devices to the epidermis, the gluing of anti-adhesion barriers for surgery and the adhesion of synthetic onlays or inlays to the cornea. Conventional surgical adhesives are often not suitable for a wide range of adhesive applications. Currently cyanoacrylates and fibrin glues are used clinically as soft tissue adhesives. However the brittleness of the cured adhesives, the potential toxicity of their biodegradation products and the lack of control over cure time are the major drawbacks of cyanoacrylates.

Further, a variety of different methods for the bonding of devices to tissue have been disclosed in the prior art. For example, U.S. Pat. No. 5,354,336 describes a method for sealing lenticules onto a corneal surface comprising the steps of placing the lenticule to the correct position, applying a polymerizable collagen composition onto the lenticule and the corneal surface to form a collagen coating over the lenticule and the corneal surface and polymerizing the coating in the presence of an initiator thereby sealing the lenticule onto the corneal surface. However said glues have not yet proven satisfactory mainly because of severe handling problems. For example, the surgeon must mix the glue components shortly prior to use. Once the premixing has taken place, only a limited time period is available for using the glue depending on the glue's specific curing time; this puts time-pressure on the surgeon. Following the attachment of the lenticule onto the cornea, excessive glue has to be removed carefully otherwise glue residues may inhibit the normal function of biological tissue. Further disadvantages of the known glues are, for example, insufficient mechanical stability and adhesive duration.

Polymers comprising one or more perfluoroalkylpolyether units and one or more different charged units, in a non-porous or particularly in a porous form, are discussed in U.S. Pat. No. 6,225,367. These polymers are stated to have an improved wettability and cell growth ability.

It had been found that polymers located in or on the stroma of the eye interfere less with the biological processes of their environment when they are porous (eg, pores of around 100 nm)—see for example the disclosure of patent application WO 95/13764. It is believed that porous polymers permit the flow of nutrients, including oxygen, or at least reduce the inhibition of flow of such nutrients. It is believed that different nutrients may flow both towards and away from outer surface of the eye. Such nutrient flow is important to reducing impact on the biological processes of the eye. However, a disadvantage associated with such porous materials is a tendency for them to gather deposits within their pores (when in situ). To counter this disadvantage, it has been found that the inclusion of a charged monomeric group (such as a zwitter-ionic group) in the formation of the polymer significantly reduces the deposits in the pores, and hence cloudiness of the material in situ. U.S. Pat. No. 6,225,367 describes a polymer where the zwitter-ionic monomer is preferably 3 to 10% (w/w) of the final polymerizable composition. Polymers for corneal onlays must also support cell growth across their surface, a characteristic known as "cell growth ability". This is important for, in particular, intraocular applications as well as other biological applications.

It has been found, in practice, that the poor miscibility between charged monomers and hydrophobic monomers (such as PFPE monomers) limits the proportion of charged, or zwitterionic, monomer incorporated into the polymer. The method discussed in U.S. Pat. No. 6,225,367 is exemplified by polymers with a zwitter-ionic content of less than about 12% (w/w) where the zwitter-ionic monomeric units are in methanol (being a typical solvent for zwitterions at 50% w/w) given the need for the zwitter-ionic units to form a stable emulsion with the PFPE monomeric units from which to form (ie, polymerise) the polymer. Optimal polymer performance (cell growth ability and transparency maintenance) usually required a zwitter-ionic monomeric content of less than 10%. However, a disadvantage of these polymers is the lengthy, complex and time-consuming process required to hydrate the polymer after its formation. Polymer hydration is important for biological applications. As described in U.S. Pat. No. 6,225,367, the polymer must be gradually hydrated through a series of solvents in which the portion of water relative to ethanol is steadily increased. This is clinically difficult or impracticable.

Reference to any prior art in the specification is not, and should not be taken as, an acknowledgment or any form of suggestion that this prior art forms part of the common general knowledge in Australia or any other country.

It will be understood that the term "comprises" or its grammatical variants as used in this specification and claims is equivalent to the term "includes" and is not to be taken as excluding the presence of other elements or features.

Surprisingly, it now has been found that biomedical devices, in particular cornea onlays and inlays comprising a suitable biocompatible bulk material, may be attached conveniently to living tissue if they comprise porous polymers with higher zwitterion content. Moreover, corneal onlays and inlays which are easier to affix in place can be made from such polymers to which certain reactive groups are covalently attached.

According to one form of the invention, there is provided a polymer comprising one or more macromonomer units and one or more charged units, the charged units being more than 12% (w/w) of the polymer. Preferably, the charged units are zwitter-ionic units.

In another form of the invention, there is provided a polymer comprising one or more macromonomer units and one or more charged units, the polymer having been polymerised from an emulsion containing the charged units in aqueous solution.

The proportion of charged unit in the polymer may be measured conveniently on a weight/weight basis, as given above. This is based on the monomeric units in the final polymer product. In other cases, molar % is useful to define the proportion of charged units. In one embodiment of this invention, the polymer of the present invention, the charged unit is at least 48 molar % of the polymer, regardless of the percentage by weight. In another embodiment, the charged unit is at least 36 molar % and at least 12% (w/w).

Preferably, the macromonomer unit is one or a mixture of those described below. More preferably, the macromonomer is selected from the group consisting of polysiloxane, perfluoroalkylpolyether (PFPE), fluorinated poly(meth)acrylate, polyalkyl (meth)acrylate, polyolefin and fluorinated polyolefin, more preferably perfluoroalkylpolyether (PFPE), In another form of the invention, there is provided a process for coating a polymer of the invention with an adhesive comprising the steps of
(a) if the polymer does not have functional groups on its surface, providing the polymer with surface functional groups on its surface,
(b) covalently coupling the surface functional groups of the polymer with a natural or synthetic polymer comprising co-reactive groups, and
(c) covalently coupling a multifunctionally active compound having at least one functional group that is co-reactive to the co-reactive groups of the natural or synthetic polymer, and is of the formula:

$$R_{13}\text{-}D\text{-}R_{12} \quad (21),$$

wherein
D is a bivalent organic radical, which is unsubstituted or substituted by one or more carboxy or carboxy derivative groups;
$R_{12}$ is a carboxy derivative group; and
$R_{13}$ is a further reactive group selected from the group consisting of a carboxy, carboxy derivative, isocyanato, isothiocyanato and epoxy group.

In another preferred embodiment, there is provided a biomedical device having a surface comprising a polymer as described above and a coating comprising carboxy derivative groups covalently attached to at least part of the surface.

It has been found that a polymer with a high equilibrium water content (for example, polymers formed from emulsions with high porogen content) above 60% are mechanically weak compared to those with a low EWC (about 25%). It is suspected (without being bound by any particular theory or mode of action) that the reduced strength is due to the increased water content. As a result, in a preferred embodiment of the invention, a cross-linking agent is added to provide increased cross-linking and therefore strength of the polymer.

The present invention therefore in one aspect relates to a biomedical device comprising
(a) a biocompatible organic bulk material and
(b) a coating comprising carboxy derivative groups covalently attached to at least part of the bulk surface.

In one embodiment of the invention there is provided a biomedical device comprising a polymer such as biocompatible organic bulk material, having functional groups on its surface, and covalently coupling the functional groups on the surface of the device with a natural or synthetic polymer comprising co-reactive groups to the surface functional groups, and covalently coupling a multifunctionally activated compound comprising at least one carboxy derivative group and at least one additional functional group that is co-reactive to the co-reactive groups of said natural or synthetic polymer.

Another preferred group of polymers which may act as bulk materials are those conventionally used for the manufacture of biomedical devices, e.g. contact lenses, intraocular lenses or artificial cornea, which are not hydrophilic per se. Such materials are known to the skilled artisan and may comprise for example polysiloxanes, perfluoropolyethers, fluorinated poly(meth)acrylates or equivalent fluorinated polymers derived e.g. from other polymerizable carboxylic acids, polyalkyl (meth)acrylates or equivalent alkylester polymers derived from other polymerizable carboxylic acids, or fluorinated polyolefines, such as fluorinated ethylene propylene, or tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another preferred group of biocompatible polymers are those being conventionally used for the manufacture of biomedical devices, e.g. contact lenses, which are hydrophilic per se, since hydrophilic groups, e.g. carboxy, carbamoyl, sulfate, sulfonate, phosphate, amine, ammonium or hydroxy groups, are inherently present in the material. Such materials are known to the skilled artisan and comprise for example polyhydroxyethyl acrylate, polyhydroxyethyl methacrylate (HEMA), polyvinyl pyrrolidone (PVP), polyacrylic acid, polymethacrylic acid, polyacrylamide, poly-N,N-dimethyl acrylamide (DMA), polyvinyl alcohol, copolymers for example from two or more monomers from the group hydroxyethyl acrylate, hydroxyethyl methacrylate, N-vinyl pyrrolidone, acrylic acid, methacrylic acid, acrylamide, N,N-dimethyl acrylamide, vinyl alcohol, vinyl acetate and the like, polyalkylene glycols such as polyethylene glycols, polypropylene glycols or polyethylene/polypropylene glycol block copolymers. Typical examples are e.g. Polymacon, Tefilcon, Methafilcon, Deltafilcon, Bufilcon, Phemfilcon, Ocufilcon, Focofilcon, Etafilcon, Hefilcon, Vifilcon, Tetrafilcon, Perfilcon, Droxifilcon, Dimefilcon, Isofilcon, Mafilcon, Nelfilcon or Atlafilcon.

An even more preferred group of bulk materials are, for example, porous polymers with improved wettability and cell growth ability as described in WO 97/35906 or in WO 00/15686. Particular preferred polymers comprise one or more perfluoroalkylpolyether (PFPE) units and one or more charged units selected from the group consisting of zwitterionic units and a mixture of anionic and cationic units.

Preferred PFPE units are of formula $$-OCH_2CF_2O(CF_2CF_2O)_x(CF_2O)_yCF_2CH_2O- \quad (1)$$

wherein the $CF_2CF_2O$ and $CF_2O$ units may be randomly distributed or distributed as blocks throughout the chain and wherein x and y may be the same or different such that the molecular weight of the perfluorinated polyether is in the range of from 242 to 8000, preferably from 242 to 4000. Preferably x in formula (1) is in the range of from 0 to 20, more preferably in the range from 8 to 12, and y is in the range from 0 to 25, more preferably in the range from 10 to 14. Even more preferred, x and y in formula (1) are both different from zero such that x is in the range of from 1 to 20, more preferably in the range from 8 to 12, and y is in the range from 1 to 25, more preferably in the range from 10 to 14. Commercially available PFPE diol often contains small amounts of $-(CF_2)_nO-$ units (where n=3 or 4). This is not significant for the invention and such macromonomers are included within the scope of the invention.

In a particularly preferred embodiment, the PFPE macromonomer is end capped with a polymerisable group (which provides added strength to the polymer through increased cross-linking). One suitable endcap is isocyanatoethyl methacrylate, which can be added by the method described in Chaouk H. et al, J. Appl. Polym. Sci., 2001, 80, 1756.

The charged units of the preferred bulk materials are ionic or zwitter-ionic units, for example those of formula

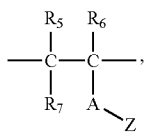

(2)

wherein either
(i) two of the three variables $R_5$, $R_6$ and $R_7$ are hydrogen and the third one is hydrogen, carboxy, carboxymethyl or $C_1$-$C_4$-alkyl; or
(ii) $R_5$ and $R_6$ together with the adjacent carbon atoms form a 5- to 7-membered cycloaliphatic or heterocyclic ring and $R_7$ is hydrogen; or
(iii) $R_5$ and $R_6$ are each hydrogen and $R_7$ and A together with the adjacent carbon atoms form a 5- to 7-membered cycloaliphatic or heterocyclic ring; or
(iv) $R_5$ and $R_7$ are each hydrogen and $R_6$ and A together with the adjacent carbon atom form a 5- to 7-membered cycloaliphatic or heterocyclic ring;

A is a direct bond or a carbonyl, carbonate, amide, ester, dicarboanhydride, dicarboimide, urea or urethane functional group; and Z is an aliphatic, cycloaliphatic or heterocyclic moiety comprising an anionic group or a cationic group or one anionic and one cationic group each.

A group of preferred units of formula (2) corresponds to formula

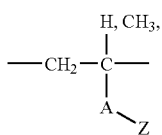

(2a)

wherein A is a direct bond or an above-mentioned functional group, preferably a carbonyl, ester or amide functional group and more preferably an ester group —C(O)—O—.

Suitable anionic groups of the moiety Z are, for example, —COO$^-$, —SO$_3^-$, —OSO$_3^-$, —OPO$_3$H$^-$, —OPO$_2^-$OR$_{11}$ or bivalent —O—PO$_2^-$—O—, wherein $R_{11}$ is, for example, $C_1$-$C_{12}$-alkyl, preferably $C_2$-$C_8$-alkyl and in particular $C_3$-$C_6$-alkyl; preferably a group —SO$_3^-$, —OPO$_2^-$OR$_{11}$ or a bivalent group —O—PO$_2^-$—O—, wherein $R_{11}$ is as defined above; and in particular a group —SO$_3^-$.

Suitable cationic groups of the moiety Z are for example a group —NRR'R"$^+$ or a bivalent group —NRR'$^+$—, wherein R, R' and R" may be the same or different and are each independently of the other, for example, hydrogen or $C_1$-$C_{24}$-alkyl, preferably hydrogen or $C_1$-$C_4$-alkyl and most preferably each methyl or ethyl. Two or more R groups may together form a carbocycle or heterocycle. A single or double bond may exist between the nitrogen and one or more of the R groups.

A group of preferred moieties Z are cationic ones wherein Z comprises one of the above-mentioned cationic groups. Another group of preferred moieties Z are anionic ones wherein Z comprises one of the above-mentioned anionic groups. Z is more preferably a zwitter-ionic moiety which comprises one of the above-mentioned anionic and cationic groups each.

The moiety Z is for example unfluorinated or fluorinated $C_2$-$C_{30}$-alkyl, preferably unfluorinated $C_2$-$C_{12}$-alkyl, and more preferably unfluorinated $C_3$-$C_8$-alkyl, which is in each case uninterrupted or interrupted by —O— and substituted and/or interrupted by one or two of the above-mentioned anionic and cationic groups. Z is preferably $C_2$-$C_{12}$-alkyl and even more preferably $C_3$-$C_8$-alkyl which is substituted and/or interrupted by one of the above-mentioned anionic and cationic groups each.

Z as a cycloaliphatic or heterocyclic moiety is, for example, a radical of formula $$-[(alk)-(R_9)_s]_t-R_{10} \qquad (3),$$

wherein (alk) is $C_1$-$C_{12}$-alkylene, preferably $C_1$-$C_4$-alkylene, s is 0 or 1, t is 0 or preferably 1, $R_9$ is for example —O— or —NH—, and $R_{10}$ is a 5- to 7-membered cycloaliphatic or heterocyclic ring, preferably a 5- or 6-membered heterocyclic ring, which is in each case substituted and/or interrupted by one or two of the above-mentioned anionic and cationic groups. Z is preferably a zwitter-ionic moiety of formula (3), wherein (alk) and t have the above-given meanings and $R_9$ is a heterocyclic 5- or 6-membered ring comprising a bivalent group —NRR'$^+$— and one of the above mentioned anionic groups, preferably a carboxy group.

Preferred charged units are zwitter-ionic units of formula (2a), wherein A is a carbonyl, ester or amide group, Z is $C_2$-$C_{12}$-alkyl which is substituted by —NRR'R"$^+$, —COO$^-$, —SO$_3^-$, —OSO$_3^-$, —OPO$_2^-$OR$_{11}$, or —OPO$_3$H$^-$ and/or is interrupted by a group —NRR'$^+$— or —O—PO$_2^-$—O—, R, R' and R" are each independently of the other hydrogen or $C_1$-$C_{12}$-alkyl and $R_{11}$ is $C_1$-$C_{12}$-alkyl, with the proviso that Z contains one anionic and one cationic group each.

A preferred group of zwitter-ionic units corresponds to the above formula (2a), wherein -A-Z is a radical of formula —C(O)O-alk-NRR'$^+$-alk'-An$^-$ (3a) or —C(O)O-alk-O—PO$_2^-$—O-alk'-NRR'R"$^+$ (3b), wherein R, R' and R" may be the same or different and are each independently of the other hydrogen or $C_1$-$C_{12}$-alkyl, preferably $C_1$-$C_4$-alkyl and more preferably methyl or ethyl; alk and alk' may be the same or different and are each independently of the other $C_1$-$C_{12}$-alkylene, preferably $C_1$-$C_8$-alkylene, more preferably $C_1$-$C_6$-alkylene and most preferably $C_1$-$C_4$-alkylene; and An$^-$ is an anionic group —COO$^-$, —SO$_3^-$, —OSO$_3^-$, —OPO$_2^-$OR$_{11}$ or —OPO$_3$H$^-$, preferably —COO$^-$, —OPO$_2^-$OR$_{11}$ or —SO$_3^-$, more preferably —OPO$_2^-$OR$_{11}$ or —SO$_3^-$ and most preferably —SO$_3^-$, wherein $R_{11}$ is $C_1$-$C_{12}$-alkyl, preferably $C_2$-$C_8$-alkyl or in particular $C_3$-$C_6$-alkyl. An even more preferred group of zwitter-ionic units corresponds to the above formula (3a), wherein the above-given meanings and preferences apply to the variables contained therein.

In a further embodiment of the invention the polymer making up the bulk material comprises a mixture of anionic and cationic units, for example, each of formula (2a), wherein for A and Z the above given meanings and preferences apply, with the proviso that the anionic units Z comprise one of the above given anionic groups, and the cationic units comprise one of the above given cationic groups.

The preferred bulk materials are obtainable, for example, by copolymerizing one or more macromonomers comprising at least one PFPE unit and at least one zwitter-ionic monomer or a precursor thereof, and, if a zwitter-ionic monomer precursor has been used, converting the precursor units into charged units after the copolymerization reaction.

Preferred macromonomers having at least one perfluoropolyether unit include, but are not limited to, those of formula (4), (5) and (6) as specified hereinafter:

$$Q\text{-}(PFPE\text{-}L)_{n-1}\text{-}PFPE\text{-}Q \quad (4),$$

$$Q\text{-}B\text{-}(L\text{-}B)_n\text{-}T \quad (5),$$

$$Q\text{-}PFPE\text{-}L\text{-}M\text{-}L\text{-}PFPE\text{-}Q \quad (6),$$

wherein in these formulae:

Q may be the same or different and is a polymerizable group,

PFPE is a divalent residue of formula (1) as hereinbefore defined,

L is a difunctional linking group;

n is at least 1;

each B may be the same or different and is a difunctional block of molecular weight in the range of from 100 to 4000 and wherein at least one B is a perfluorinated polyether of formula (1);

T is a univalent terminal group which is not polymerisable by free radicals but which may contain other functionality; and M is a residue from a difunctional polymer or copolymer comprising silicone repeat units of formula (7) having a molecular weight preferably in the range of from 180 to 6000 and end functionality as described below

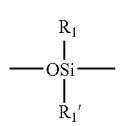

(7)

wherein $R_1$ and $R_1'$ may be the same or different and are selected from the group consisting of hydrogen, alkyl, aryl and halosubstituted alkyl and in particular $C_1$-$C_8$-alkyl, phenyl and $C_1$-$C_8$-haloalkyl. $R_1$ and $R_1'$ are preferably methyl.

In the above formulae (4), (5) and (6), respectively, the following definitions apply:

It is preferred that n is in the range of from 1 to 5, more preferably n is in the range of from 1 to 3. Macromonomers where n is 1 are particularly preferred.

Q is a polymerizable group which preferably comprises an ethylenically unsaturated moiety which can enter into a free radical polymerization reaction. Preferably Q is a group of the formula $$P_1\text{—}(Y)_m\text{—}(R_2\text{—}X_1)_p\text{—} \quad (8)$$

wherein $P_1$ is a free-radically-polymerizable group;

Y is —CONHCOO—, —CONHCONH—, —OCONHCO—, —NHCONHCO—, —NHCO—, —CONH—, —NHCONH—, —COO—, —OCO—, —NHCOO— or —OCONH—;

m and p, independently of one another, are 0 or 1;

$R_2$ is a divalent radical of an organic compound having up to 20 carbon atoms; and $X_1$ is, for example, a direct bond or a group —NHCO— or —CO—.

A free-radically-polymerizable group $P_1$ is, for example, alkenyl, alkenylaryl or alkenylarylenealkyl having up to 20 carbon atoms. Examples of alkenyl are vinyl, allyl, 1-propen-2-yl, 1-buten-2-, -3- and -4-yl, 2-buten-3-yl, and the isomers of pentenyl, hexenyl, octenyl, decenyl and undecenyl. Examples of alkenylaryl are vinylphenyl, vinylnaphthyl or allylphenyl. An example of alkenylarylenealkyl is o-, m-, or p-vinylbenzyl.

$P_1$ is preferably alkenyl or alkenylaryl having up to 12 carbon atoms, particularly preferably alkenyl having up to 8 carbon atoms, in particular alkenyl having up to 4 carbon atoms.

Y is preferably —COO—, —OCO—, —NHCONH—, —NHCOO—, —OCONH—, NHCO— or —CONH—, particularly preferably —COO—, —OCO—, NHCO— or —CONH—, and in particular, —COO— or —CONH—.

$X_1$ is preferably —NHCO—.

In a preferred embodiment, the indices, m and p, are not simultaneously zero.

$R_2$ is preferably alkylene, arylene, a saturated bivalent cycloaliphatic group having 6 to 20 carbon atoms, arylenealkylene, alkylenearylene, alkylenearylenealkylene or arylenealkylenearylene.

Preferably, $R_2$ is a divalent radical having up to 12 carbon atoms, particularly preferably a divalent radical having up to 8 carbon atoms. In a preferred embodiment, $R_2$ is furthermore alkylene or arylene having up to 12 carbon atoms. A particularly preferred embodiment of $R_2$ is lower alkylene, in particular lower alkylene having up to 4 carbon atoms.

It is particularly preferred that Q be selected from the group consisting of acryloyl, methacryloyl, styryl, acrylamido, acrylamidoalkyl, acryloyloxyalkylaminocarbonyl or any substituted derivatives thereof. Most preferably Q is a compound of formula (8) wherein $P_1$ is alkenyl of up to 4 carbon atoms, Y is —COO—, $R_2$ is alkylene of 2 to 4 carbon atoms, $X_1$ is —NHCO— and m and p are each one, and is in particular the radical $CH_2$=$C(CH_3)$—$C(O)O$—$(CH_2)_2$—NH—$C(O)$—. This end-capping is believed to assist in the preparation of the emulsion from which the polymer is formed.

The above given radicals Y and $X_1$ are to be understood that in case of Y the left bond is directed to the radical $P_1$ and the right bond is directed to the group ($R_2$—$X_1$) or PFPE, and in case of $X_1$ the left bond is directed to $R_2$ and the right bond is directed to PFPE.

The linking group L may be the bivalent residue of any difunctional moiety able to react with hydroxyl. Suitable precursors to L are α,ω-diepoxides, α,ω-diisocyanates, α,ω-diisothiocyanates, α,ω-diacylhalides, α,ω-dithioacylhalides, α,ω-dicarboxylic acids, α,ω-dithiocarboxylic acids, α,ω-dianhydrides, α,ω-dithioisocyanates, α,ω-dilactones, α,ω-dialkylesters, α,ω-dihalides, α,ω-dialkylethers, α,ω-dihydroxymethylamides. It is preferred that the linking group be a bivalent residue —C(O)—NH—$R_3$—NH—C(O)— of a diisocyanate or the corresponding residue of a dithioisocyanate, wherein $R_3$ is a divalent organic radical having up to 20 carbon atoms.

The divalent radical $R_3$ is, for example, alkylene, arylene, alkylenearylene, arylenealkylene or arylenealkylenearylene having up to 20 carbon atoms, a saturated bivalent cycloaliphatic group having 6 to 20 carbon atoms or cycloalkylenealkylenecycloalkylene having 7 to 20 carbon atoms.

In a preferred embodiment, $R_3$ is alkylene, arylene, alkylenearylene, arylenealkylene or arylenealkylenearylene having up to 14 carbon atoms or a saturated divalent cycloaliphatic group having 6 to 14 carbon atoms. In a particularly preferred embodiment, $R_3$ is alkylene or arylene having up to 12 carbon atoms or a saturated bivalent cycloaliphatic group having 6 to 14 carbon atoms.

In a preferred embodiment, $R_3$ is alkylene or arylene having up to 10 carbon atoms or a saturated bivalent cycloaliphatic group having 6 to 10 carbon atoms.

In a particularly preferred meaning, $R_3$ is a radical derived from a diisocyanate, for example from hexane 1,6-diisocyanate, 2,2,4-trimethylhexane 1,6-diisocyanate, tetramethylene diisocyanate, phenylene 1,4-diisocyanate, toluene 2,4-diisocyanate, toluene 2,6-diisocyanate, m- or p-tetramethylxylene diisocyanate, isophorone diisocyanate or cyclohexane 1,4-diisocyanate.

Aryl is a carbocyclic aromatic radical which is unsubstituted or substituted preferably by lower alkyl or lower alkoxy. Examples are phenyl, tolyl, xylyl, methoxyphenyl, t-butoxyphenyl, naphthyl and phenanthryl.

Arylene is preferably phenylene or naphthylene, which is unsubstituted or substituted by lower alkyl or lower alkoxy, in particular 1,3-phenylene, 1,4-phenylene or methyl-1,4-phenylene, 1,5-naphthylene or 1,8-naphthylene.

A saturated bivalent cycloaliphatic group is preferably cycloalkylene, for example cyclohexylene or cyclohexylene (lower alkylene), for example cyclohexylenemethylene, which is unsubstituted or substituted by one or more lower alkyl groups, for example methyl groups, for example trimethylcyclohexylenemethylene, for example the bivalent isophorone radical.

For the purposes of the present invention, the term "lower" in connection with radicals and compounds, unless defined otherwise, denotes, in particular, radicals or compounds having up to 8 carbon atoms, preferably having up to 4 carbon atoms.

Lower alkyl has, in particular, up to 8 carbon atoms, preferably up to 4 carbon atoms, and is, for example, methyl, ethyl, propyl, butyl, tert-butyl, pentyl, hexyl or isohexyl.

Alkylene has up to 12 carbon atoms and can be straight-chain or branched. Suitable examples are decylene, octylene, hexylene, pentylene, butylene, propylene, ethylene, methylene, 2-propylene, 2-butylene, 3-pentylene, and the like.

Lower alkylene is alkylene having up to 8 carbon atoms, particularly preferably up to 4 carbon atoms. Particularly preferred meanings of lower alkylene are propylene, ethylene and methylene.

The arylene unit in alkylenearylene or arylenealkylene is preferably phenylene, unsubstituted or substituted by lower alkyl or lower alkoxy, and the alkylene unit therein is preferably lower alkylene, such as methylene or ethylene, in particular methylene. These radicals are therefore preferably phenylenemethylene or methylenephenylene.

Lower alkoxy has, in particular, up to 8 carbon atoms, preferably up to 4 carbon atoms, and is, for example, methoxy, ethoxy, propoxy, butoxy, tert-butoxy or hexyloxy.

Arylenealkylenearylene is preferably phenylene(lower alkylene)phenylene having up to 8, in particular up to 4, carbon atoms in the alkylene unit, for example phenyleneethylenephenylene or phenylenemethylenephenylene.

Some examples of preferred diisocyanates from which bivalent residues L are derived include trimethylhexamethylenediisocyanate (TMHMDI), isophorone diisocyanate (IPDI), methylene diphenyl diisocyanate (MDI) and 1,6-hexamethylenediisocyanate (HMDI).

The blocks B may be monomeric, oligomeric or polymeric. The molecular weights and chemical composition of each block B may be the same or different, provided that they fall within the molecular weight range specified above. The blocks B may be hydrophobic or hydrophilic, provided that at least one of the blocks is of formula (1). Other suitable blocks B may be derived from poly(alkylene oxides). When one or more of the blocks B is hydrophilic, these blocks are particularly preferably derived from poly(alkylene oxides), more preferably from poly(lower alkylene oxides), most preferred from the polyethylene glycols. it is most preferred that the B blocks are selected from blocks of formula (1) and poly(alkylene oxides), provided that at least one of the blocks is of formula (1). In two very preferred embodiments of the invention there are two B blocks in a macromonomer of formula (5) which are either both of formula (1), or one of which is of formula (1) while the other is derived from a poly(alkylene oxide), preferably from a poly(lower alkylene oxide), most preferred from polyethylene glycols. "Derived from a poly(alkylene oxide)" in the context of the definition of the B blocks means that such a B block differs from a poly(alkylene oxide) in that the two terminal hydrogens have been abstracted from such poly(alkylene oxide). In order to exemplify this, B denotes, if derived from a polyethylene glycol, —$(OCH_2CH_2)_aO$— wherein a is the index indicating the number of repeating ethyleneoxy groups.

The terminal group T is a univalent terminal group which is not polymerizable by free radicals but which may contain other functionality. Preferred terminal groups are hydrogen, alkyl, substituted alkyl, aryl or substituted aryl. More preferred groups T are hydrogen, lower alkyl and phenyl.

Suitable substituents for Q or T may be selected from: alkyl, alkenyl, alkynyl, aryl, halo, haloalkyl, haloalkenyl, haloalkynyl, haloaryl, hydroxy, alkoxy, alkenyloxy, aryloxy, haloalkoxy, haloalkenyloxy, haloaryloxy, amino, alkylamino, alkenylamino, alkynylamino, arylamino, acyl, aroyl, alkenylacyl, arylacyl, acylamino, alkylsulphonyloxy, arylsulphenyloxy, heterocyclyl, heterocycyloxy, heterocylamino, haloheterocyclyl, alkoxycarbonyl, alkylthio, alkylsulphonyl, arylthio, arylsulphonyl, aminosulphonyl, dialkylamino and dialkylsulphonyl, having up to 10 carbon atoms.

The difunctional polymer from which M is derived contains an independently selected terminal functionality at each end which may react with the precursor of the linking group L so that a covalent linkage is formed. The preferred terminal functionality is hydroxyl or amino. Such functionality may be joined to the siloxane units in M by means of an alkylene group or other non reactive spacer. Preferred terminal moieties are hydroxyalkyl, hydroxyalkoxyalkyl and alkylamino. Especially preferred hydroxyalkyls are hydroxypropyl and hydroxybutyl; especially preferred hydroxyalkoxyalkyls are hydroxyethoxyethyl and hydroxyethoxypropyl. Preferred $R_1$ and $R_1'$ groups are methyl.

Preferred M residues in formula (6) as specified above are of formula

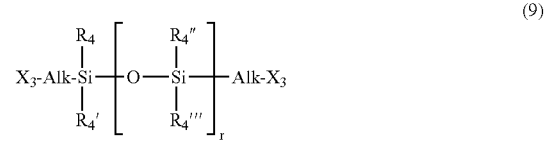

(9)

where r is an integer from 5 to 100; Alk is alkylene having up to 20 carbon atoms, uninterrupted or interrupted by oxygen; the radicals $R_4$, $R_4'$, $R_4''$ and $R_4'''$, independently of one another, are alkyl, aryl or halosubstituted alkyl; and $X_3$ is —O— or —NH—.

In a preferred meaning, r is an integer from 5 to 70, particularly preferably 8 to 50, in particular 10 to 28.

In a preferred meaning, the radicals $R_4$, $R_4'$, $R_4''$ and $R_4'''$ are, independently of one another, lower alkyl having up to 8 carbon atoms, particularly preferably lower alkyl having up to 4 carbon atoms, especially lower alkyl having up to 2 carbon atoms. In a further particularly preferred embodiment $R_4$, $R_4'$, $R_4''$ and $R_4'''$ are each methyl.

Alkylene interrupted by oxygen is preferably lower alkylene-oxy-lower alkylene having up to 6 carbons in each of the two lower alkylene moieties, more preferably lower alkylene-oxy-lower alkylene having up to 4 carbons in each of the two lower alkylene moieties, examples being ethylene-oxy-ethylene or ethylene-oxy-propylene.

Halosubstituted alkyl is preferably lower alkyl substituted by one or more, especially up to three, halogens such as fluoro, chloro or bromo, examples being trifluoromethyl, chloromethyl, heptafluorobutyl or bromoethyl.

A preferred macromonomer is of formula (4) wherein n is in the range of from 2 to 5, L is a bivalent residue —C(O)—NH—$R_3$—NH—C(O)— of a diisocyanate wherein $R_3$ is alkylene, arylene, alkylenearylene, arylenealkylene or arylenealkylenearylene having up to 14 carbon atoms or a saturated divalent cycloaliphatic group having 6 to 14 carbon atoms, and Q is a compound of formula (8) wherein $P_1$ is alkenyl of 2 to 4 carbon atoms, Y is —COO—, $R_2$ is alkylene of 1 to 4 carbon atoms, $X_1$ is —NHCO— and m and p are each 1.

A preferred macromonomer of formula (4) is one in which n is in the range of from 2 to 5, L is the bivalent residue derived from trimethylhexamethylene diisocyanate (TMHMDI) and Q is the residue derived from isocyanatoethyl methacrylate.

A preferred embodiment of this invention is directed to a macromonomer of formula (10a):

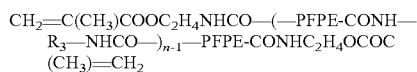

wherein PFPE is a perfluorinated polyether of formula (1) as herein defined, wherein x is in the range of from 8 to 10 and y is in the range of from 10 to 14, n>1, and $R_3$ is alkylene or arylene having up to 12 carbon atoms or a saturated bivalent cycloaliphatic group having 6 to 14 carbon atoms.

In a preferred embodiment of the present invention there is provided a macromonomer of formula (10b):

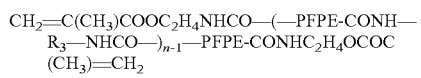

wherein PFPE is a perfluorinated polyether of formula (1) as herein defined, n>1, $R_3$ is the trimethylhexamethylene component of TMHMDI, and wherein x is in the range of from 8 to 10 and y is in the range of from 10 to 14.

In a preferred embodiment of the present invention there are provided macromonomers of formula (5) which correspond to formulae (11) to (14)

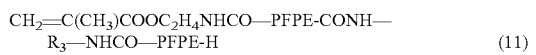 (11)

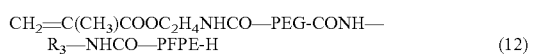 (12)

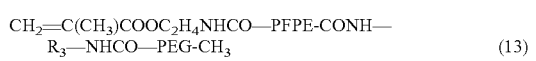 (13)

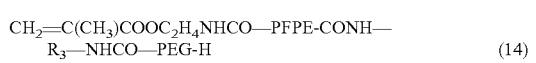 (14)

wherein PFPE is of formula (1) wherein x and y are as defined hereinbefore, $R_3$ is alkylene, arylene, alkylenearylene, arylenealkylene or arylenealkylenearylene having up to 14 carbon atoms or a saturated divalent cycloaliphatic group having 6 to 14 carbon atoms, and PEG is the divalent radical of a polyethylene glycol. Preferably PEG has a molecular weight in the range of from 200 to 2000.

In an even more preferred embodiment of the present invention there are provided macromonomers of formulae (15) to (18):

 (15)

 (16)

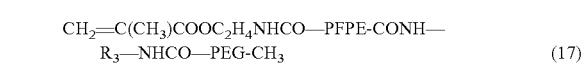 (17)

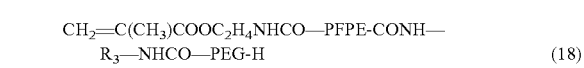 (18)

wherein PFPE is of formula (1) wherein x and y are as defined hereinbefore, wherein $R_3$ is the trimethylhexamethylene component of TMHMDI, and PEG is the divalent radical of a polyethylene glycol. Preferably PEG has a molecular weight in the range of from 200 to 2000. It is also preferred in this embodiment that x is 10 and y is 12.

A preferred macromonomer of formula (6) is one in which the molecular weight of the perfluorinated polyether is in the range of from 800 to 4,000, L is the bivalent residue derived from trimethylhexamethylene diisocyanate (TMHMDI) and Q is the residue derived from isocyanatoethyl methacrylate. It is particularly preferred that the molecular weight of the perfluorinated polyether is about 2,000 and the molecular weight of M is about 1,000.

A preferred macromonomer of the present invention is of formula (19):

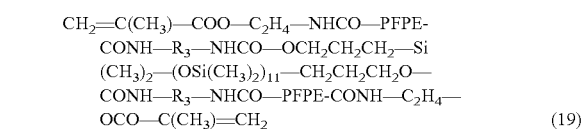 (19)

wherein PFPE is of formula (1), x in formula (1) is 10 and y is 12, and $R_3$ is the trimethyhexamethylene component of TMHMDI (trimethylhexamethylene diisocyanate).

The polymers of the invention may be composed of one or more than one different macromers, for example, of formulae (4), (5) or (6). The PFPE macromonomers of the invention and their synthesis are known e.g. from PCT applications WO 96/31546 or WO 97/35906.

A suitable charged monomer unit which may be introduced in the copolymerization reaction, is, for example, represented by formula

 (2b)

wherein for $R_5$, $R_6$, $R_7$, A and Z the above-given meanings and preferences apply.

The charged units or zwitterions may be formed after polymerization. A suitable polymerizable precursor of a charged monomer is represented, for example, by formula

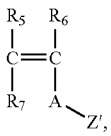

(2c)

wherein for $R_5$, $R_6$, $R_7$ and A the above-given meanings and preferences apply, and Z' is, for example, an aliphatic, cycloaliphatic or heterocyclic moiety comprising a reactive group, for example a hydroxy group, an amino group or a protected amino group, in particular a group —NRR' or —NR—C(O)O-tert.-butyl, wherein for R and R' the above given meanings and preferences apply. A preferred group of monomers of the formula (2c) is represented by the formula

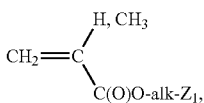

(2c')

wherein $Z_1$ is hydroxy or an amino or protected amino group, in particular a radical —NRR' or —NR—C(O)O-tert.-butyl, and for alk, R and R' the above-given meanings and preferences apply in each case.

The components of the formula (2c) or (2c') may be converted into a charged form either before or after the polymerization reaction, for example, by an acid treatment or quaternization of the amino group with an alkyl halide, optionally after removal of the protective group. Zwitter-ionic moieties are obtained, for example, by quaternizing the amino group with a compound comprising an anionic group such as —COOH, —SO$_3$H, —OSO$_3$H or —OPO$_3$H$_2$ or a suitable salt thereof. Suitable quaternization reagents are, for example, alkyl sultones such as propyl sultone or haloalkyl carboxylic acids such as iodo acetic acid. Components of formula (2c) or (2c') comprising a radical Z' that contains a hydroxy or amino group may also be converted into a charged form, for example, by coupling said hydroxy or amino group with a pre-existing charged compound, for example with a zwitter-ionic compound such as an amino acid including peptides and proteins.

The charged monomers are known compounds or may be obtained according to processes known per se. For example, the zwitter-ionic monomers may be obtained in situ just before the polymerization reaction by reacting a compound of the above formula (2c') wherein $Z_1$ is an amino group with a suitable quaternization reagent, for example an alkyl sultone or haloalkyl carboxylic acid.

In the preferred composition of the copolymers making up the bulk material, the proportion by weight of the PFPE macromonomer(s) is in the range of 99.5 to 50%, in particular in the range of 98 to 60%, preferably in the range of 98 to 70% and most preferably about 80%, based on the total of polymerizable components. The proportion of the zwitter-ionic monomer is, for example, in the proportion of 0.5 to 49%, in particular 12 to 49%, preferably 12 to 25% and most preferably about 20% by weight, based on the total of polymerizable components.

In a further embodiment, in addition to the PFPE macromonomer(s) and the zwitter-ionic monomer units or its precursors, further comonomers comprising one or more ethylenically unsaturated groups may be incorporated into the polymerization mixture which can enter into a reaction to form the bulk materials of the invention. It is preferred that the ethylenically unsaturated group be selected from the group consisting of acryloyl, methacryloyl, styryl, acrylamido, acrylamidoalkyl, or urethanemethacrylate, or any substituted derivatives thereof.

A comonomer present in the polymer making up the bulk material can be hydrophilic or hydrophobic or a mixture thereof. Suitable comonomers are, in particular, those which are usually used in the production of contact lenses and biomedical materials. A hydrophobic comonomer is taken to mean a monomer which typically gives a homopolymer which is insoluble in water and can absorb less than 10% by weight of water. Analogously, a hydrophilic comonomer is taken to mean a monomer which typically gives a homopolymer which is soluble in water or can absorb at least 10% by weight of water.

Suitable hydrophobic comonomers are, without limitation thereto, $C_1$-$C_{18}$alkyl and $C_3$-$C_{18}$cycloalkyl acrylates and methacrylates, $C_3$-$C_{18}$alkylacrylamides and -methacrylamides, acrylonitrile, methacrylonitrile, vinyl $C_1$-$C_{18}$alkanoates, $C_2$-$C_8$alkenes, $C_2$-$C_{18}$haloalkenes, styrene, (lower alkyl)styrene, lower alkyl vinyl ethers, $C_2$-$C_{10}$perfluoroalkyl acrylates and methacrylates and correspondingly partially fluorinated acrylates and methacrylates, $C_3$-$C_{12}$perfluoroalkylethyl-thiocarbonylaminoethyl acrylates and methacrylates, acryloxy- and methacryloxyalkylsiloxanes, N-vinylcarbazole, $C_1$-$C_{12}$alkyl esters of maleic acid, fumaric acid, itaconic acid, mesaconic acid and the like. Preference is given, for example, to acrylonitrile, $C_1$-$C_4$alkyl esters of vinylically unsaturated carboxylic acids having 3 to 5 carbon atoms or vinyl esters of carboxylic acids having up to 5 carbon atoms.

Examples of suitable hydrophobic comonomers are methyl acrylate, ethyl acrylate, propyl acrylate, isopropyl acrylate, cyclohexyl acrylate, 2-ethylhexyl acrylate, methyl methacrylate, ethyl methacrylate, propyl methacrylate, butyl acrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyltoluene, vinyl ethyl ether, perfluorohexylethyl-thiocarbonylaminoethyl methacrylate, isobornyl methacrylate, trifluoroethyl methacrylate, hexafluoroisopropyl methacrylate, hexafluorobutyl methacrylate, tris-trimethylsilyloxysilylpropyl methacrylate (hereinafter: Tris methacrylate), tris-trimethylsilyloxysilylpropyl acrylate (hereinafter: Tris acrylate), 3-methacryloxy propylpentamethyldisiloxane and bis(methacryloxypropyl)tetramethyldisiloxane. Preferred examples of hydrophobic comonomers are methyl methacrylate, Tris acrylate, Tris methacrylate and acrylonitrile.

Suitable hydrophilic comonomers are, without this being an exhaustive list, hydroxyl-substituted lower alkyl acrylates and methacrylates, acrylamide, methacrylamide, (lower alkyl)acrylamides and -methacrylamides, ethoxylated acrylates and methacrylates, hydroxyl-substituted (lower alkyl) acrylamides and -methacrylamides, hydroxyl-substituted lower alkyl vinyl ethers, N-vinylpyrrole, N-vinyl-2-pyrrolidone, 2-vinyloxazoline, 2-vinyl-4,4'-dialkyloxazolin-5-one, 2- and 4-vinylpyridine, allyl alcohol and the like. Preference is given to N-vinyl-2-pyrrolidone, acrylamide, methacrylamide, hydroxyl-substituted lower alkyl acrylates and methacrylates and hydroxy-substituted (lower alkyl)acrylamides and -methacrylamides. Examples of suitable hydrophilic comonomers are hydroxyethyl methacrylate (HEMA), hydroxyethyl acrylate, hydroxypropyl acrylate, acrylamide, methacrylamide, N,N-dimethylacrylamide (DMA), allyl alcohol, vinylpyridine, glycerol methacrylate, N-(1,1-dimethyl-3-oxobutyl)acrylamide, N-vinyl-2-pyrrolidone (NVP), and the like. Preferred hydrophilic comonomers are 2-hydroxyethyl methacrylate, N,N-dimethylacrylamide and N-vinyl-2-pyrrolidone.

As stated hereinbefore, suitable comonomers include fluorine- and silicon-containing alkyl acrylates and hydrophilic comonomers, which may be selected from a wide range of materials available, and mixtures thereof. Particularly preferred comonomers include dihydroperfluoroalkyl acrylates, such as dihydroperfluorooctyl acrylate and 1,1-dihydroperfluorobutyl acrylate, trihydroperfluoroalkyl acrylates, tetrahydroperfluoroalkyl acrylates, tris(trimethylsilyloxy)propyl methacrylate or acrylate, and amine-containing comonomers, such as N,N-dimethylaminoethyl methacrylate, N,N-dimethylacrylamide and N,N-dimethyl-aminoethyl-acrylamide. The preferred range for addition of individual comonomers into the formulation is from 0 to 60% by weight and most preferably 0 to 40% by weight of the formulation. In a preferred embodiment of the invention, the polymer is prepared in the absence of a comonomer.

The bulk material network can, if desired, be reinforced by addition of a crosslinking agent, that is not a PFPE polymer, for example by a polyunsaturated crosslinking comonomer. Examples of typical crosslinking comonomers are allyl (meth)acrylate, lower alkylene glycol di(meth)acrylate, poly (lower alkylene) glycol di(meth)acrylate, lower alkylene di(meth)acrylate, divinyl ether, divinyl sulfone, di- and trivinylbenzene, trimethylolpropane tri(meth)acrylate, pentaerythritol tetra(meth)acrylate, bisphenol A di(meth)acrylate, methylenebis(meth)acrylamide, triallyl phthalate and diallyl phthalate. Polyunsaturated perfluoroalkyl crosslinkers of formula

$$Q\text{-}CH_2\text{---}(CF_2)_q\text{---}CH_2\text{-}Q \qquad (22),$$

wherein for Q the above given meanings and preferences apply, and q is an integer of, for example, from 1 to 20 and preferably from 1 to 12, are the preferred additional crosslinking comonomers.

In one preferred embodiment, the polymer is strengthened by the addition of a crosslinking agent to the polymerisable components. Two preferred cross-linking agents are prepared by reacting octofluoro-1,6-hexane diol with either isocyanoctoethyl methacrylate or methacryoyl chloride and triethylamine.

If a crosslinking comonomer is used, the amount used is in the range of from 0.01 to 40% of the expected total weight of polymer, preferably the comonomer is in the range of 0.1 to 30%, and more preferably in the range of 0.1 to 20%. In one preferred embodiment, the polymerization mixture does not contain a crosslinking monomer.

The preferred bulk materials of the invention may be obtained by copolymerizing one or more PFPE macromonomers, one or more charged monomers or a suitable precursor thereof and optional further comonomers and/or additives to afford a transparent polymer in the presence of a suitable initiator. Standard methods well known in the art for effecting polymerization may be utilized, with free radical polymerization being preferred. Free radical polymerization can be simply carried out by radiating (using ultra-violet light) monomer mixtures containing a UV initiator, such as benzoin methylether, in an appropriate container or vessel. The mixture is irradiated for a sufficient time to enable polymerization between monomers to take place. Alternatively, thermal initiation using a thermal initiator such as azobisisobutyronitrile, can be employed. If a precursor of the zwitter-ionic monomer is used, the copolymer after the irradiation may be treated with a suitable reagent in order to convert the precursor units into zwitter-ionic units. Examples of this are given in U.S. Pat. No. 6,225,367, especially Examples 11 and 12.

The polymerization mixture can be converted to a polymer neat or in the presence of one or more solvents. While the structure of the components of the polymerization mixture has the most significant effect on the resulting modulus, the choice of solvent and comonomer also has an effect. Useful solvents include those selected from the following classes: esters, alcohols, ethers, and halogenated solvents. Fluorinated solvents are particularly useful and their use in combination with other solvents (in ratios varying from 1:9 to 9:1) from the classes above is especially desirable. Solvent concentrations of between 0-99% w/w, particularly 30-80% w/w, especially 55% in the polymerization mixture are desirable. Preferred solvents include acetates, particularly isopropyl acetate and tert-butyl acetate, 2-(trifluoromethyl)-2-propanol, chlorofluoroalkanes, particularly trichlorotrifluoroethane, and perfluorinated alkanes, such as perfluoro-1,3-dimethylcyclohexane, 2,2,3,3-tetrafluor-1-propanol, 2',3',4',5',6'-pentafluoroacetophenone, 1,1,1-trifluoro-3,4-pentadione, 2',3',4',5', 6'-pentafluorobenzyl alcohol and the like. A particular preferred solvent is water or an aqueous solution comprising, for example, one or more organic solvents, for example a $C_1$-$C_4$-alkanol such as methanol or ethanol, or a fluorinated alkane. Water may be 1 to 70% w/w, preferably 2 to 50% w/w and particularly preferably 3 to 30% w/w, in each case based on the entire formulation.

The polymers of the invention are preferably porous substrates. Porosity may be provided by the inherent porosity of the material. Alternatively, pores may be introduced into the polymers by various procedures such as those disclosed in PCT applications WO 00/15686. In case of porous bulk materials it is preferred to incorporate a polar solvent, for example water, a $C_1$-$C_4$-alkanol, and/or a surfactant, preferably a fluorinated surfactant, into the polymerization mixture. The use of surfactants is an effective means of controlling the size and density of the pores. Non-ionic surfactants containing fluorine are preferred. Particularly preferred surfactants include commercially available fluorinated surfactants such as Zonyl (DuPont) and Fluorad (3M). Zonyl surfactants, which are made of a perfluorinated hydrophobic tail and hydrophilic poly(ethylene oxide) head group, are a particularly preferred surfactant for use in the process of the present invention.

Particular preferred bulk materials according to the invention are those obtainable by copolymerizing one or more macromonomers comprising at least one PFPE unit, wherein the above-given meanings and preferences apply, and at least one zwitter-ionic monomer or a precursor thereof, wherein again the above-given meanings and preferences apply, in an aqueous solution and, if a zwitter-ionic monomer precursor has been used, converting the precursor units into charged units after the copolymerization reaction. A particular preferred reaction medium in this context is an aqueous solution comprising a $C_1$-$C_4$-alkanol, in particular methanol or ethanol, a fluorinated surfactant and optionally a fluorinated alkane.

The surface of the bulk material may inherently contain functional groups or may be provided with covalently attached functional groups, for example, by plasma deposition. The method of coating a surface by plasma deposition is known to the skilled artisan and is described in, e.g. WO 98/52620 and WO 00/29548. Typical examples of reactive groups being introduced to the surface of the bulk material by plasma surface preparation include aldehyde groups, amino groups, hydroxy groups, carboxy groups, carbonyl groups, sulfonic acid groups, sulfonyl chloride groups and groups able to be replaced by amino or hydroxy groups, such as halo groups. Aldehyde groups, thiol groups, amino groups, hydroxy groups and carboxy groups are preferred. Other known methods of introducing functional groups include dipping the bulk material. The functional groups may be provided on some of the surface or all of the surfaces of the bulk material. This may be achieved by techniques such as masking.

Examples of natural or synthetic polymer are cell-adhesive glycoproteins like collagens (various types), fibronectin, vitronectin, laminin, poly(ethyl imine), amino dextran, PAMAM dendrimers, poly(allyl amine), poly(vinyl alcohol), poly(arylic acid) and poly(methacrylic acid). Collagen and collagen-like proteins are preferred. The coupling of cell-adhesive glycoproteins to plasma polymers covalently bound to the underlying bulk material is known and described, for example, in WO 00/29548.

Suitable multifunctionally activated compounds suitable for use with this invention are, for example, carboxylic halides, for example —COCl or —COBr; carboxylic anhydrides; lactones; carboxylic amides; or preferably carboxylic esters. A preferred group of carboxy derivative groups are esters, in particular activated esters or amides.

An activated ester or amide is, for example, a radical of formula

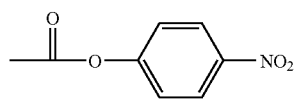 (20a)

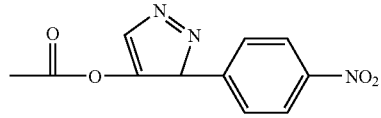 (20b)

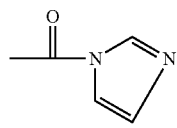 (20c)

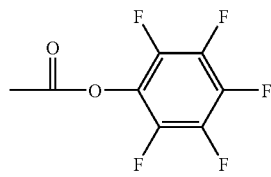 (20d)

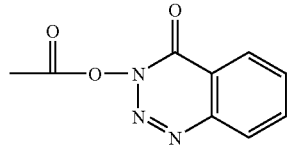 (20e)

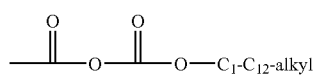 (20f)

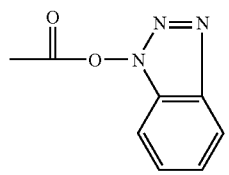 (20g)

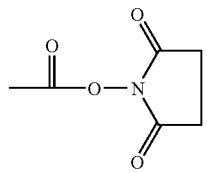 (20h)

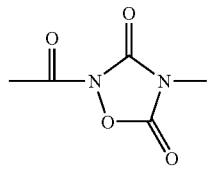 (20i)

A preferred carboxy derivative group according to the invention is an activated ester group of formula (20g), (20e) or, in particular, of formula (20h).

Multifunctional compounds are, for example, compounds of formula $$R_{13}\text{-}D\text{-}R_{12} \quad (21),$$

wherein

D is a bivalent organic radical, which may be substituted, for example, by one or more carboxy or carboxy derivative groups;

$R_{12}$ is a carboxy derivative group; and $R_{13}$ is a further reactive group, for example a carboxy, a carboxy derivative, isocyanato, isothiocyanato or epoxy group.

Examples of bivalent organic radicals D are, for example, an optionally branched $C_1$-$C_{12}$-alkylene; a radical of dendrimer or star bust polymer; a radical of a polyethylene glycol; a radical of a polyvinyl alcohol, for example, a polyvinyl alcohol with pendant polymerisable groups as described in WO 96/24075; or a radical of a hyperbranched polyester resin as described by M. Johansson and A. Hult in Journal of Coatings Technology, 67, No. 849, 35 (1995). D is preferably a bivalent radical of a polyethylene glycol, for example a radical of formula —$CH_2$—$CH_2$—(O—$CH_2$—$CH_2$)$_f$—, wherein f is an integer of, for example, from 2 to 250.

In one embodiment, the multifunctionally activated compound is polyethylene glycol that is di-substituted with succinimidyl propionate, succinimidyl succinate or succinimidyl succinimide, or the known derivatives of these functional groups.

$R_{12}$ is a carboxy derivative group, wherein the above given meanings and preferences apply. $R_{13}$ is independently preferably a carboxy derivative group, wherein the above given meanings and preferences apply. Most preferably, $R_{12}$ and $R_{13}$ are identical.

The method of attaching a multifunctionally activated compound of formula (21) to a bulk material surface provided with a natural or synthetic polymer comprising co-reactive functional groups depends on the nature of the reactive groups being present in compound (21) and of the natural or synthetic polymer. The reactions are known per se, for example, from textbooks of organic chemistry.

For example, in case that a compound of formula (21) with a carboxy, amide or ester group $R_{13}$ is to be coupled to a natural or synthetic polymer containing amino, thiol or hydroxy groups, the reaction may be carried out under the conditions that are customary for ester or amide formation. It is preferred to carry out the esterification or amidation reaction in the presence of an activating agent, for example N-ethyl-N'-(3-dimethyl aminopropyl) carbodiimide (EDC), N-hydroxy succinimide (NHS) or N,N'-dicyclohexyl carbodiimide (DCC).

In case that a compound of formula (21) with an anhydride group $R_{13}$ is to be coupled to a natural or synthetic polymer containing amino, thiol or hydroxy groups the reaction may be carried out as described in organic textbooks, for example in an aprotic solvent, for example one of the above-mentioned aprotic solvents, at a temperature from room temperature to about 100° C.

In case that a compound of formula (21) with an activated ester or amide group $R_{13}$ is to be coupled to the surface of a bulk material or to a natural or synthetic polymer containing amino, thiol or hydroxy groups, the reaction may be carried out, for example, at room temperature or at elevated temperature, for example at about 20 to 100° C., in an aprotic medium.

In case that a compound of formula (21) with an isocyanato group $R_{13}$ is to be coupled to a natural or synthetic polymer containing amino or hydroxy groups, the reaction may be carried out in an inert organic solvent such as acetonitrile, an optionally halogenated hydrocarbon, for example petroleum ether, methylcyclohexane, toluene, chloroform, methylene chloride and the like, or an ether, for example diethyl ether, tetrahydrofurane, dioxane, or a more polar solvent such as DMSO, DMA, N-methylpyrrolidone or even a lower alcohol or water, at a temperature of from 0 to 100° C., preferably from 0 to 50° C. and particularly preferably at room temperature, optionally in the presence of a catalyst, for example a tertiary amine such as triethylamine or tri-n-butylamine, 1,4-diazabicyclooctane, or a tin compound such as dibutyltin dilaurate or tin dioctanoate. In addition, the reaction of the isocyanato groups with amino groups may also be carried out in an aqueous solution in the absence of a catalyst. It is advantageous to carry out the above reactions under an inert atmosphere, for example under a nitrogen or argon atmosphere.

In case that a compound of formula (21) with an epoxy group $R_{13}$ is to be coupled to a natural or synthetic polymer containing amino, thiol or hydroxy groups, the reaction may be carried out, for example, at room temperature or at elevated temperature, for example at about 20 to 100° C., in an aprotic medium using a base catalyst, for example Al(O—$C_1$-$C_6$-alkyl)$_3$ or Ti(O—$C_1$-$C_6$-alkyl)$_4$.

Moreover, biomedical devices according to the invention comprising a preferred bulk material, that is a bulk material obtainable by copolymerizing a macromonomer comprising at least one PFPE unit and a zwitter-ionic monomer in an aqueous solution, offer the additional advantage, that unlike other hydrophobic materials, for example those disclosed in WO 00/15686, they may be hydrated very easily. Accordingly, the biomedical devices of the invention may be dehydrated after their preparation and stored for extended periods without loss of adhesive activity. Such a biomedical device, for example an onlay, is then immediately ready for use, by just placing it in water for a short period, typically for about 1 to 10 minutes and particularly for about 2 minutes, which is sufficient to re-hydrate both the bulk material and the coating (so as to re-activate the hydrolytically unstable functional groups of the multifunctionally activated compound). All of these advantages naturally apply not only to contact lenses but also to other biomedical mouldings according to the invention as mentioned before.

In a further preferred form of the invention, biomedical devices (such as corneal inlays and onlays or lenticules) are formed from a polymer as described above, and then dried and stored in anhydrous conditions. This maintains the multifunctionally activated compounds' unreacted reactive groups such that they can bond to tissue upon implantation or affixation of the device to tissue after re-hydration to increase polymer chain mobility.

The biomedical devices of the present invention such as in particular corneal onlays and inlays may be fixed on the cornea by just placing the device in intimate contact with the corneal tissue for a certain time period, for example for about 5 to 30 minutes and especially for 10 to 20 minutes. Such onlays and inlays are easier to handle, since the use thereof does not involve, for example, a premixing of glue components or time pressure upon the surgeon due to specific curing times of the glue components. In addition, no tedious removal of excess glue after fixing onto the cornea is necessary, and the previous problem of inhibition of overgrowth by glue residues does not exist.

Preferably, the cornea is previously prepared for the attachment of an onlay, for example, by removing the epithelial cell layers of the cornea by scraping and/or washing the eye, for example, with ethanol/water mixtures. Ideally the cornea surface and the lenticule are dried with surgical sponges or the like. It is desirable to minimise the fluid and air between the lenticule and the cornea surface. Excess fluid and air may be removed by applying pressure across the membrane using a rolling action with a surgical instrument. Such onlays provide a new route towards implanting a corneal onlay onto a cornea which is easy to perform, does not affect the wearers vision, and is safe. In particular, a mechanically stable fixation of the implant on the cornea is obtained which lasts for a period of time sufficient for normal biological function to recover after surgery. This may include the chance to allow the epithelial cells to recover, grow over the implant and thus fix it in a persistent manner.

The invention is particularly suitable for corneal inlays where cell growth ability is less important. Cell growth ability may be impeded by higher charged unit content, such as over 10% w/w, although cell growth ability may be regained by surface modification (eg, binding of collagen). In other words, a higher surface charge (ie, higher zwitterion or charged monomer concentration) may reduce cell growth, but this disadvantage can be overcome by surface modifying the polymer (eg, collagen or PFPE coating). The inlay may be implanted using known techniques. For example, an incision may be made in the stroma, into which the re-hydrated inlay is placed. The inlay then attaches to the stroma through reaction of the re-activated functional groups of the multifunctionally activated compound with no additional material being required. Polymers with charged unit content of around 20% are useful for this application.

It will be appreciated that the effect of charged unit content on the properties of a polymer of the invention will depend on the charged unit's molecular weight, the number of charges, density, location in the polymer (distribution about the bulk and surface) and other factors. For convenience, in the examples, the proportion of charged unit in a polymer is expressed as parts per weight.

The present invention is further described by the following non-limiting examples. If not specified otherwise, all parts are by weight. Temperatures are in degrees Celsius.

EXAMPLES 1-42

Preparation of a Self-Hydrating PFPE Material

The following formulations were prepared in a glass vial furnished with a stirrer. The components were added in order of decreasing hydrophilicity and mixed well, prior to the addition of the photoinitiator. After the addition of the photoinitiator (Darocur 1173), the mixing was continued for a further five minutes. The resulting solutions were then placed in polypropylene moulds and polymerised for 3 hours under the irradiation of broad spectrum UV lamps (1 mW/cm$^{-2}$). The polymers (20 mm diameter disc 50 to 250 microns thick) were removed from the mold and placed through a general extraction procedure to remove any unpolymerised components. This procedure consists of a 2×24h soaking in a fluorinated solvent such as Vertrel XF (DuPont), TCTFE (Aldrich) or HFE 7100 (3M), then 2×24 hr immersion in isopropyl acetate and subsequent immersion for 2×24 h in methanol. The polymers of Examples 1 to 4 were then hydrated by a graded solvent change from methanol to ethanol, 75% ethanol/water, 50% ethanol/water overnight, 25% ethanol/water, then pure water or saline. This assists in extraction of unpolymerised monomers, solvents and surfactants.

Examples 1 to 4 used a combination of Part A and Part B for polymerisation as follows:

| Part A consisted of (parts by weight): | |
|---|---|
| PFPE macromonomer #1 | 4.5 |
| PFPE macromonomer #2 | 0.5 |
| Ethanol | 2.5 |
| PFDMCH | 3.0 |

Part B consisted of a 50% (w/w) solution of [2-(methacryloyloxy)ethyl]dimethyl(3-sulfopropyl)-ammonium inner salt (zwitterion) in water.

| | Example | | | |
|---|---|---|---|---|
| | 1 | 2 | 3 | 4 |
| Part A | 1.749 | 1.819 | 1.821 | 1.749 |
| Part B | 0.143 | 0.085 | 0.086 | 0.140 |
| Surfactant | Zonyl FSK | Zonyl FSA | Zonyl FSO100 | Zonyl FSN100 |
| | 0.1841 | 0.290 | 0.143 | 0.158 |
| Darocur 1173 | 0.0024 | 0.0038 | 0.0033 | 0.0024 |
| EWC (%) | 27.5 | 32.1 | 21.0 | 19.1 |
| Optical Clarity (%) | 95.6 | 94.5 | 94.1 | 93.8 |
| Porosity (A$_{280}$) | 0.815 | 1.073 | 0.607 | 0.361 |

Explanation of Abbreviations:

PFPE macromonomer #1: perfluorinated macromer obtained by endcapping a perfluoropolyether diol (Ausimont, Italy, M$_w$=2000) with isocyanatoethyl methacrylate as described in Chaouk H. et al., J. Appl. Polym. Sci., 2001, 80, 1756;

PFPE macromonomer #2: perfluorinated macromer obtained by endcapping a perfluoropolyether diol (Ausimont, Italy, M$_w$=1000) with isocyanatoethyl methacrylate as described in Chaouk H. et al., J. Appl. Polym. Sci., 2001, 80, 1756;

Zonyl FSK, FSA, FSO100 and FSN100=non-ionic fluorinated surfactants (DuPont);

Darocur®1173=photoinitiator (Ciba Speciality Chemicals).

PFDMCH=perfluorodimethylcyclohexane

Equilibrium water contents (EWC) (expressed as percentages) and porosity measurements are measured as reported by Chaouk H. et al, J. Appl. Polym. Sci., 2001, 80, 1756.

Optical haze (%) is measured using a Gardner PG-5500 digital photometric unit. Optical clarity is calculated by subtracting optical haze from 100%.

Examples 5-30 had the following compositions and characteristics:

| | Example | | | | | |
|---|---|---|---|---|---|---|
| | 5 | 6 | 7 | 8 | 9 | 10 |
| PFPE#1 | 0.9 | 0.9 | 0.9 | 0.9 | 0.9 | 0.9 |
| PFPE#2 | 0.1 | 0.1 | 0.1 | 0.1 | 0.1 | 0.1 |
| Zwitterion | 0.02 | 0.05 | 0.1 | 0.1 | 0.2 | 0.2 |
| TFPr | 0.6 | 0.6 | 0.6 | 0.6 | 0.6 | 0.6 |
| methanol | 0.5 | 0.5 | 0.55 | 0.45 | 0.25 | 0.45 |
| H$_2$O | 0.05 | 0.05 | 0.05 | 0.1 | 0.3 | 0.1 |
| FSO-100 | 0.08 | 0.08 | 0.08 | 0.08 | 0.45 | 0.2 |
| Darocur 1173 | 0.09 | 0.09 | 0.09 | 0.09 | 0.09 | 0.09 |
| EWC (%) | 47.2 | 48.74 | 53.61 | 50.23 | 48.14 | 49.33 |
| Wet Optical Clarity (%) | 92.32 | 96 | 91.85 | 93.24 | 96.47 | 95.78 |
| BSA Perm (A$_{280}$) | 1.06 | 1.063 | 0.788 | 1.115 | 0.882 | 0.978 |

| | Example | | | | | |
|---|---|---|---|---|---|---|
| | 11 | 12 | 13 | 14 | 15 | 16 |
| PFPE#1 | 0.9 | 0.9 | 0.9 | 0.9 | 0.9 | 0.9 |
| PFPE#2 | 0.1 | 0.1 | 0.1 | 0.1 | 0.1 | 0.1 |
| Zwitterion | 0.2 | 0.2 | 0.2 | 0.2 | 0.2 | 0.2 |
| TFPr | 0.6 | 0.6 | 0.6 | 0.6 | 0.6 | 0.6 |
| methanol | 0.75 | 1.5 | 1.5 | 0.25 | 1.75 | 1 |
| H$_2$O | 0.25 | 0.5 | 0.5 | 1.75 | 0.25 | 1 |
| FSO-100 | 0.35 | 0.4 | 0.4 | 2.25 | 0.38 | 0.5 |
| Darocur 1173 | 0.09 | 0.09 | 0.09 | 0.09 | 0.09 | 0.09 |
| EWC (%) | 61.1 | n.t. | 71.95 | 57.84 | 76.65 | 58.33 |
| Wet Optical Clarity (%) | 93 | 92.2 | 95 | n.t. | 95 | 93 |
| BSA Perm (A$_{280}$) | 1.361 | n.t. | n.t. | n.t. | n.t. | n.t. |

| | Example | | |
|---|---|---|---|
| | 17 | 18 | 19 |
| PFPE#1 | 1.0 | 0.9 | 0.9 |
| PFPE#2 | — | 0.1 | 0.1 |
| Zwitterion | 0.2 | 0.2 | 0.2 |
| TFPr | 0.6 | 0.6 | 0.6 |
| methanol | 1.5 | 1.5 | 1.5 |
| H$_2$O | 0.5 | 0.5 | 0.5 |
| FSO-100 | 0.43 | 0.43 | 0.4 |
| Crosslinker (1) | 0.25 | 0.5 | 1.25 |
| Darocur 1173 | 0.10 | 0.09 | 0.09 |
| EWC (%) | 72.1 | 66.8 | 48.51 |
| Wet Optical Clarity (%) | 53.5 | 57.8 | 88.8 |

| | Example | | |
|---|---|---|---|
| | 20 | 21 | 22 |
| PFPE#1 | 0.9 | 0.9 | 0.9 |
| PFPE#2 | 0.1 | 0.1 | 0.1 |
| Zwitterion | 0.2 | 0.2 | 0.2 |
| TFPr | 0.6 | 0.6 | 0.6 |
| methanol | 1.5 | 1.5 | 1.5 |
| H$_2$O | 0.5 | 0.5 | 0.5 |
| FSO-100 | 0.4 | 0.4 | 0.4 |
| Crosslinker (2) | 0.05 | 0.10 | 0.5 |
| Darocur 1173 | 0.09 | 0.09 | 0.09 |
| EWC (%) | 65.7 | 71.4 | 78.5 |
| Wet Optical Clarity (%) | 68.5 | 45.5 | 70.7 |

| | Formulation | | |
|---|---|---|---|
| | 23 | 24 | 25 |
| PFPE#1 | 0.9 | 0.9 | 0.9 |
| PFPE#2 | 0.1 | 0.1 | 0.1 |
| Zwitterion | 0.2 | 0.2 | 0.2 |

-continued

|  | | | |
|---|---|---|---|
| TFPr | 0.6 | 0.6 | 0.6 |
| methanol | 1.5 | 1.5 | 1.5 |
| $H_2O$ | 0.5 | 0.5 | 0.5 |
| FSO-100 | 0.4 | 0.4 | 0.4 |
| EGDMA | 0.02 | 0.05 | 0.10 |
| Darocur 1173 | 0.09 | 0.09 | 0.09 |
| EWC (%) | 69.9 | 68.3 | 67.5 |
| Wet Optical Clarity (%) | 93 | 88.4 | 81.1 |

| | Example | | | | |
|---|---|---|---|---|---|
| | 26 | 27 | 28 | 29 | 30 |
| PFPE#1 | 0.9 | 0.9 | 0.9 | 0.9 | 0.9 |
| PFPE#2 | 0.1 | 0.1 | 0.1 | 0.1 | 0.1 |
| Zwitterion | 0.05 | 0.05 | 0.05 | 0.3 | 0.4 |
| TFPr | 0.6 | 0.6 | 0.6 | 0.6 | 0.6 |
| methanol | 0.30 | 0.75 | 0.75 | 0.25 | 0.25 |
| $H_2O$ | 0.25 | 0.1 | 0.25 | 0.3 | 0.3 |
| FSO-100 | 0.2 | 0.2 | 0.2 | 0.6 | 1.0 |
| Darocur 1173 | 0.09 | 0.09 | 0.09 | 0.09 | 0.09 |
| EWC (%) | 43.3 | 53.2 | 52.2 | 46.7 | 52.8 |
| Wet Optical Clarity (%) | 98.9 | 96.4 | 94.2 | n.t. | n.t. |
| BSA Perm ($A_{280}$) | | 0.566 | 1.231 | 1.018 | n.t. | n.t. |

| | Example | | | | | |
|---|---|---|---|---|---|---|
| | 31 | 32 | 33 | 34 | 35 | 36 |
| PFPE#1 | 0.5 | 0.5 | 0.5 | 0.5 | 0.5 | 0.5 |
| Monomer A | 0.025 | — | 0.0125 | — | 0.0246 | 0.0125 |
| Monomer B | — | 0.025 | — | 0.0125 | 0.0275 | 0.127 |
| TFPr | 0.3 | 0.3 | 0.3 | 0.3 | 0.3 | 0.3 |
| methanol | 0.25 | 0.25 | 0.25 | 0.27 | 0.25 | 0.25 |
| $H_2O$ | 0.035 | 0.035 | 0.024 | 0.035 | 0.026 | 0.032 |
| FSO-100 | 0.10 | 0.10 | 0.10 | 0.10 | 0.10 | 0.10 |
| Darocur 1173 | 0.045 | 0.045 | 0.045 | 0.045 | 0.045 | 0.045 |
| EWC (%) | 48.7 | 50.2 | 47.0 | 49.2 | 51.6 | 48.3 |
| Wet Optical Clarity (%) | 94.8 | 97.7 | 96.8 | 97.4 | 97.5 | 97.4 |

| | Example | | | | | |
|---|---|---|---|---|---|---|
| | 37 | 38 | 39 | 40 | 41 | 42 |
| PFPE#1 | 0.90 | 0.90 | 0.91 | 0.90 | 0.90 | 0.91 |
| PFPE#2 | 0.10 | 0.10 | 0.10 | 0.11 | 0.11 | 0.11 |
| Monomer A | 0.15 | — | 0.076 | — | 0.15 | 0.076 |
| Monomer B | — | 0.18 | — | 0.089 | 0.18 | 0.089 |
| TFPr | 0.60 | 0.60 | 0.60 | 0.061 | 0.61 | 0.60 |
| methanol | 0.25 | 0.25 | 0.25 | 0.25 | 0.25 | 0.26 |
| $H_2O$ | 0.30 | 0.32 | 0.29 | 0.31 | 0.34 | 0.30 |
| FSO-100 | 0.46 | 0.45 | 0.45 | 0.46 | 0.46 | 0.46 |
| Darocur 1173 | 0.09 | 0.09 | 0.09 | 0.09 | 0.09 | 0.09 |
| EWC (%) | 53.5 | 51.6 | 49.7 | 50.0 | 38.3 | 47.5 |
| Wet Optical Clarity (%) | 97.4 | 98.1 | 98.2 | 98.1 | 91.2 | 97.2 |
| BSA Perm ($A_{280}$) | 0.720 | 0.798 | 0.865 | 0.877 | 0.433 | 0.711 |

PFPE#1 and PFPE#2 are as for Examples 1 to 4.

Crosslinker (1) is prepared by reacting octafluoro-1,6-hexanediol (Fluorochem Ltd, UK) with isocyanatoethyl methacrylate (IEM).

Crosslinker (2) is prepared by reacting octafluoro-1,6-hexanediol (Fluorochem Ltd, UK) with methacryoyl chloride and triethylamine.

Ethyleneglycol dimetharcylate (EGDMA) (Aldrich, USA).

Zwitterion is [2-(methacryloyloxy)ethyl]dimethyl(3-sulfopropyl)-ammonium inner salt (Aldrich).

TFPr=tetrafluoropropanol (Aldrich, USA)

Monomer A is [2-(methacryloyloxy)ethyl]trimethyl ammonium chloride (Aldrich, USA)

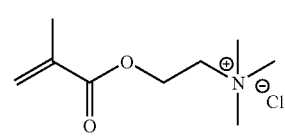

(23)

Monomer B is 3-sulfopropyl methacrylate (Aldrich, USA)

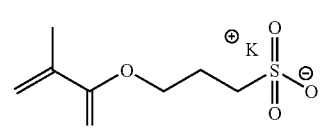

(24)

EXAMPLE 43

Cell Growth Ability

Cell attachment (bovine corneal epithelial) and tissue explant (bovine corneal) outgrowth assays for Examples 1 to 9 were measured by the method reported by Johnson G., et al., *J. Biomater. Sci. Polymer Edn.*, 1999, 10, 217-233.

The results were as follows:

| Formulation | Tissue Outgrowth (% of TCPS) | Cell Attachment (% of TCPS) |
|---|---|---|
| 1 | 130.9 | n.t. |
| 2 | 176.7 | 26.89 |
| 3 | 194.7 | 95.42 |
| 4 | 128.15 | 82.65 |
| 5 | 41.93 | 51.23 |
| 6 | 114.14 | 29.2 |
| 8 | 108.89 | 17.58 |
| 9 | 19.52 | 129.11 |

From the above examples, these novel materials showed high permeability to bovine serum albumin, are typically optically transparent, and support effective attachment and migration of corneal epithelial cells on the surface.

EXAMPLES 44

Rehydration

A selection of the Examples (1 to 11, 20 to 22, 24 and 25) were then tested for hydration after 10 minutes by immersion, such as used to hydrate hydrogels. The results were as follows:

| Formulation | Size reached at 10 minutes (% of hydrated) |
|---|---|
| 1 | 100 |
| 2 | 85 |

| Formulation | Size reached at 10 minutes (% of hydrated) |
|---|---|
| 3 | n.t. |
| 4 | n.t. |
| 5 | 72 |
| 6 | 72 |
| 7 | 100 |
| 8 | 100 |
| 9 | 86 |
| 10 | 100 |
| 11 | 100 |
| 20 | 100 |
| 21 | 100 |
| 22 | 89 |
| 24 | 100 |
| 25 | 100 |

Materials made from the formulations listed above thus had 'hydrogel-like' properties in their ease of rehydration. They can be re-hydrated from a dry state by simply placing them into water without the use of a gradient exchange process (eg, using ethanol/water mixtures of increasing water concentration) required to hydrate more hydrophobic PFPE polymers. The optical clarity and the equilibrium water contents of materials hydrated by direct hydration is within a few percentage of the optical clarity and the equilibrium water content of the materials measured after gradient exchange hydration.

EXAMPLE 45

Adhesive Surface Modification of a "Self-hydrating" Bulk Material

The formulation of Example 1 was covalently coated, both sides, with type 1 collagen according to the procedure disclosed in WO 00/29548. The collagen coated materials were then exchanged from phosphate buffered saline (PBS) to MilliQ water, then 100% ethanol and finally acetonitrile. The acetonitrile was then replaced by dry acetonitrile. 250 µl of poly(ethylene glycol) di(succinimidyl propionate) solution (582 mg, Shearwater Polymers, dissolved in 1.2 ml of dry acetonitrile) were added to each of the acetonitrile equilibrated collagen coated self-hydrating polymer samples in separate vials. After 20 minutes of incubation, 3 samples (samples 1,2,3) were evaporated to dryness using a rotary evaporator. Another 3 samples (4,5,6) had the excess crosslinker solution removed with a pipette. Dry acetonitrile (2 ml) was added to these vials and they were gently shaken before removing excess acetonitrile solution with a pipette. The three samples (samples 4,5,6) were then evaporated to dryness using a rotary evaporator. All samples were stored under vacuum over $P_2O_5$ until used, in this case seven days later, although lenticules made in this manner could be stored much longer.

EXAMPLE 46

Adhesive Testing of a "Self-hydrating" Biomedical Device

The dried surface-modified lenticules of Example 45 are hydrated by placing them in water. The use of hot water sped up the hydration process. The hydration process may be performed using PBS instead of water or aqueous mixtures. Once hydrated, the lenticules were surface dried using lint-free tissue paper and then placed on a freshly debrided bovine cornea. Excess fluid and bubbles were expelled from under the lenticule by gently wiping across the anterior surface of the lenticule. The lenticule was allowed to cure for 15 to 19 minutes before the adhesion was assessed using a vacuum tester (a detachment threshold >5.5 means that the adhesion is greater than what was able to be tested using the vacuum tester):

| Sample | hydration time (minutes) | cure time (minutes) | detachment threshold |
|---|---|---|---|
| 1 | 2 | 16 | >5.5 |
| 2 | 2 | 15 | >5.5 |
| 3 | 2 | 15 | >5.5 |
| 4 | 2 | 15 | >5.5 |
| 5 | 2 | 17 | 3.5 |
| 6 | 2 | 19 | >5.5 |

EXAMPLE 47

Effect of Collagen Coating

The formulation in Example 10 was collagen coated with type 1 bovine collagen following the method reported in WO 98/52620 and WO 00/29548. Briefly, PFPE membranes were modified using radio frequency glow discharge (rfgd) plasma polymerization of acetaldehyde (ALDRICH, 99%). The plasma conditions were Power: Load 5 Watts, Radio Frequency: 125 kHz, Monomer pressure: 0.30±0.005 Torr and Treatment time: 60 secs. Freshly deposited acetaldehyde treated membranes were placed in a 50 µg/ml solution of collagen (Vitrogen100, min. 95% bovine collagen type I, Cohesion, Palo Alto, Calif., USA) in phosphate buffered saline (PBS), pH 7.4, at 4° C. Excess $NaCNBH_3$ (SIGMA) was added and membranes incubated overnight at 4° C., then for 2 hours at room temperature.

Unmodified, acetaldehyde modified and collagen coated membranes were all tested in vitro for cell attachment (bovine corneal epithelial) and tissue explant (bovine corneal) outgrowth (method: Johnson G., et al., *J. Biomater. Sci. Polymer Edn.*, 1999, 10, 217-233).

| Membrane | Tissue Outgrowth (% of TCPS) | Cell Attachment (% of TCPS) |
|---|---|---|
| Unmodified PFPE from example 10 | 0.00 | 17.7 |
| Acetaldehyde modified PFPE from example 10 | 157.7 | 67.8 |
| Collagen coated PFPE from example 10 | 143.8 | 73.60 |

From the above examples, collagen coating and plasma modification both enhanced the biological response to the PFPE membranes.

EXAMPLE 48

In vivo Testing of PFPE Lenticules

The formulation described in Example 10 was cast into contact lens type moulds to form lenticules (4 mm diameter, 100 microns central thickness). Following the extraction and hydration process, these unmodified lenticules were implanted into New Zealand white rabbits (n=8) using a LASIK flap generated with the aid of a microkeratome. At 6 and 12 months post-implantation 3 animals were sacrificed and the eyes processed for histological examination by light and electron microscopy: Post operative monitoring of the eyes up until 12 months revealed no adverse responses in both implant and sham groups. In each of the test eyes, the inlay was maintained in position under a LASIK flap where it remained optically clear and deposit-free. Clinically, the epithelium anterior to the lenticule and stroma around the lenticule were healthy and there was no evidence of stromal melting or inflammation. Histology at the 6 and 12 month time point demonstrated a high level of biocompatibility associated with the implanted polymer lenticules.

It will be understood that the invention disclosed and defined herein extends to all alternative combinations of two or more of the individual features mentioned or evidence from the text or drawings. All of these different combinations constitute various alternative aspects of the invention.

The invention claimed is:

1. A polymer comprising (A) one or more macromonomer units selected from the group consisting of perfluoroalkylpolyether (PFPE), fluorinated poly(meth)acrylate, poly(perfluoroalkyl) (meth)acrylate, poly(fluoroalkyl) (meth)acrylamide, and fluorinated polyolefin, and (B) one or more charged units, wherein the polymer is formed from a polymerization medium containing an aqueous solution of charged units.

2. A polymer according to claim 1 in which the polymerization medium further comprises a fluorinated surfactant.

3. A polymer according to claim 1 wherein the macromonomer is perfluoroalkylpolyether (PFPE).

4. A polymer according to claim 1 in which the aqueous solution further comprises either or both an $C_1$-$C_{12}$ alkanol and $C_1$-$C_{12}$ fluoroalkanol.

5. A polymer according to claim 4 in which the aqueous solution further comprises tetrafluoropropanol.

6. A polymer according to claim 1 in which the charged units are zwitter-ionic units.

7. A polymer according to claim 1 in which the polymer is formed from an emulsion of PFPE monomeric units and an aqueous solution of charged monomer precursors, the precursors being converted into charged units after polymerization.

8. A polymer according to claim 3, wherein the PFPE units comprise $$Q\text{-}(PFPE\text{-}L)_n\text{-}1\text{-}PFPE\text{-}Q \quad (4), \text{ or}$$

$$Q\text{-}B\text{-}(L\text{-}B)_n\text{-}T \quad (5),$$

wherein Q may be the same or different and is a polymerizable group;

PFPE is a divalent residue of formula $$-OCH_2CF_2O(CF_2CF_2O)_x(CF_2O)_yCF_2CH_2O- \quad (1),$$

wherein the $CF_2CF_2O$ and $CF_2O$ units may be randomly distributed or distributed as blocks throughout the chain and wherein x and y may be the same or different such that the molecular weight of the perfluorinated polyether is in the range of from 242 to 8000, the residue optionally further comprising —$CF_2CF_2CF_2O$— and/or —$CF_2CF_2CF_2CF_2O$— units;

L is a difunctional linking group;

n is at least 1;

each B may be the same or different and is a divalent block of molecular weight in the range of from 100 to 4000 and wherein at least one B is a perfluorinated polyether of formula (1) above, and T is a univalent terminal group which is not polymerisable by free radicals but which may contain other functionality.

9. A polymer according to claim 8 in which Q is $CH_2=C(CH_3)C(O)O(CH_2)_2\text{-}NH\text{-}C(O)\text{-}$.

10. A polymer according to claim 7, wherein the charged monomer precursor is an ionic or a zwitter-ionic monomer of formula

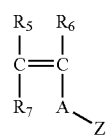

(2b)

wherein (i) two of the three variables R5, R6 and R7 are hydrogen and the third one is hydrogen, carboxy, carboxymethyl or C1-C4-alkyl and A is a direct bond or a carbonyl, carbonate, amide, ester, dicarboanhydride, dicarboimide, urea or urethane functional group; or (ii) R5 and R6 together with the adjacent carbon atoms form a 5- to 7-membered cycloaliphatic or heterocyclic ring and R7 is hydrogen and A is a direct bond or a carbonyl, carbonate, amide, ester, dicarboanhydride, dicarboimide, urea or urethane functional group; or (iii) R5 and R6 are each hydrogen and R7 and A together with the adjacent carbon atoms form a 5- to 7-membered cycloaliphatic or heterocyclic ring; or (iv) R5 and R7 are each hydrogen and R6 and A together with the adjacent carbon atom form a 5- to 7-membered cycloaliphatic or heterocyclic ring; and Z is an aliphatic, cycloaliphatic or heterocyclic moiety comprising an anionic group or a cationic group or one anionic and one cationic group each; or is a precursor thereof.

11. A polymer according to claim 1, wherein the charged units are more than 48 molar % of the polymer.

12. A polymer according to claim 11 wherein the macromonomer is perfluoroalkylpolyether (PFPE).

13. A polymer according to claim 11 in which the polymer is formed from an emulsion of PFPE monomeric units and an aqueous solution of charged monomer precursors, the precursors being converted into charged units after polymerisation.

14. A polymer according to claim 13, wherein the charged monomer precursor is an ionic or a zwitter-ionic monomer of formula

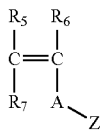 (2b)

wherein
(i) two of the three variables R5, R6 and R7 are hydrogen and the third one is hydrogen, carboxy, carboxymethyl or CI-C4-alkyl and A is a direct bond or a carbonyl, carbonate, amide, ester, dicarboanhydride, dicarboimide, urea or urethane functional group; or
(ii) R5 and R6 together with the adjacent carbon atoms form a 5- to 7-membered cycloaliphatic or heterocyclic ring and R7 is hydrogen and A is a direct bond or a carbonyl, carbonate, amide, ester, dicarboanhydride, dicarboimide, urea or urethane functional group; or
(iii) R5 and R6 are each hydrogen and R7 and A together with the adjacent carbon atoms form a 5- to 7-membered cycloaliphatic or heterocyclic ring; or
(iv) R5 and R7 are each hydrogen and R6 and A together with the adjacent carbon atom form a 5- to 7-membered cycloaliphatic or heterocyclic ring; and
Z is an aliphatic, cycloaliphatic or heterocyclic moiety comprising an anionic group or a cationic group or one anionic and one cationic group each; or is a precursor thereof.

15. A polymer according to claim 1, to which is bonded a multifunctionally activated compound of formula $$R_{13}\text{-}D\text{-}R_{12} \quad (21),$$

wherein
D is a bivalent organic radical, which is unsubstituted or substituted by one or more carboxy or carboxy derivative groups;
R12 is a carboxy derivative group; and
R13 is a further reactive group selected from the group consisting of a carboxy, carboxy derivative, isocyanato, isothiocyanato and epoxy group.

16. A polymer according to claim 15, wherein D is an optionally branched C1-C12-alkylene; a radical of a dendrimer or star-burst polymer; a radical of a polyethylene glycol; a radical of a polyvinyl alcohol; or a radical of a hyperbranched polyester resin.

17. A polymer according to claim 15, wherein D is polyethyleneglycol and $R_{12}$ and $R_{13}$ are

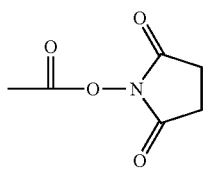

18. A polymer according to claim 1, to which is bonded one or more multifunctionally activated compounds being polyethylene glycol that is di-substituted with succinimidyl propionate, succinimidyl succinate or succinimidyl succinimide.

19. A polymer according to claim 1 further comprising a cross-linking agent.

20. A polymer according to claim 19 in which the cross-linking agent is formed by reacting octafluoro-1,6-hexanediol with either isocyanatoethyl methacrylate or methacryloyl chloride and triethylamine.

21. A process for coating a polymer according to claim 1 with an adhesive comprising the steps of
(a) if the polymer does not have surface functional groups on its surface, providing the substrate with surface functional groups on its surface,
(b) covalently coupling the surface functional groups to a natural or synthetic polymer comprising co-reactive groups, and
(c) covalently coupling a multifunctionally activated compound having at least one functional group that is co-reactive to the reactive groups of the natural or synthetic polymer, and is of the formula:

$$R_{13}\text{-}D\text{-}R_{12} \quad (21),$$

wherein
D is a bivalent organic radical, which is unsubstituted or substituted by one or more carboxy or carboxy derivative groups;
R12 is a carboxy derivative group; and
R13 is a further reactive group selected from the group consisting of a carboxy, carboxy derivative, isocyanato, isothiocyanato and epoxy group.

22. A process for coating a polymer according to claim 1 with an adhesive comprising the steps of
(a) if the polymer does not have surface functional groups on its surface, providing the substrate with surface functional groups on its surface, and
(b) covalently coupling a multifunctionally activated compound having at least one functional group that is co-reactive to the surface functional groups, and is of the formula:

$$R_{13}\text{-}D\text{-}R_{12} \quad (21),$$

wherein
D is a bivalent organic radical, which is unsubstituted or substituted by one or more carboxy or carboxy derivative groups;
R12 is a carboxy derivative group; and
R13 is a further reactive group selected from the group consisting of a carboxy, carboxy derivative, isocyanato, isothiocyanato and epoxy group.

23. A process according to claim 21, wherein the polymer is a corneal inlay, corneal onlay or lenticule.

24. A process according to claim 22, wherein the polymer is a corneal inlay, corneal onlay or lenticule.

25. A biomedical device formed from the process of claim 21.

26. A biomedical device formed from the process of claim 22.

27. A biomedical device according to claim 25, which is an ophthalmic device.

28. A biomedical device according to claim 27, which is a contact lens, intraocular lens, corneal inlay, corneal onlay, or an artificial cornea.

29. A biomedical device according to claim 27, having unreacted functional groups, the device being dehydrated to a substantially anhydrous state.

30. A biomedical device according to claim 27, wherein the polymer comprises at least one zwitter-ionic precursor.

31. A method of introducing a device to the cornea, comprising providing a dehydrated device according to claim 29, hydrating the device by immersing it in an aqueous solution or pure water and then placing the device in contact with the cornea.

32. A method according to claim 31 in which the cornea has previously been prepared for attachment by removing epithelial cell layers.

33. An intraocular lens for the implantation into or onto the cornea, comprising a polymer according to claim 1.

34. A polymer consisting essentially of (A) one or more macromonomer units selected from the group consisting of perfluoroalkylpolyether (PFPE), fluorinated poly(meth)acrylate, poly(perfluoroalkyl) (meth)acrylate, poly(fluoroalkyl) (meth)acrylamide, and fluorinated polyolefin, and (B) one or more charged units, wherein the polymer is formed from a polymerization medium containing an aqueous solution of charged units.

35. A polymer consisting essentially of perfluoroalkylpolyether (PFPE) and one or more charged units, wherein the polymer is formed from a polymerization medium containing an aqueous solution of charged units.

* * * * *